(12) United States Patent
Lieberman et al.

(10) Patent No.: US 9,309,212 B2
(45) Date of Patent: Apr. 12, 2016

(54) COMPOSITIONS AND METHODS FOR MODULATING THE ACTIVITY OF EPSTEIN-BARR NUCLEAR ANTIGEN 1

(75) Inventors: Paul M. Lieberman, Wynnewood, PA (US); Troy Messick, Upper Darby, PA (US)

(73) Assignee: The Wistar Institute, Philadelphia, PA (US)

( * ) Notice: Subject to any disclaimer, the term of this patent is extended or adjusted under 35 U.S.C. 154(b) by 0 days.

(21) Appl. No.: 14/119,541

(22) PCT Filed: May 22, 2012

(86) PCT No.: PCT/US2012/038938
§ 371 (c)(1),
(2), (4) Date: Nov. 22, 2013

(87) PCT Pub. No.: WO2012/162291
PCT Pub. Date: Nov. 29, 2012

(65) Prior Publication Data
US 2014/0113897 A1 Apr. 24, 2014

Related U.S. Application Data

(60) Provisional application No. 61/489,293, filed on May 24, 2011.

(51) Int. Cl.
| C07D 307/79 | (2006.01) |
| C07D 307/82 | (2006.01) |
| C07D 405/04 | (2006.01) |
| C07D 405/12 | (2006.01) |
| C07D 407/04 | (2006.01) |
| C07D 413/04 | (2006.01) |
| C07D 413/12 | (2006.01) |
| C07D 417/12 | (2006.01) |

(52) U.S. Cl.
CPC ............ *C07D 307/79* (2013.01); *C07D 307/82* (2013.01); *C07D 405/04* (2013.01); *C07D 405/12* (2013.01); *C07D 407/04* (2013.01); *C07D 413/04* (2013.01); *C07D 413/12* (2013.01); *C07D 417/12* (2013.01)

(58) Field of Classification Search
USPC ........................................................ 549/467
See application file for complete search history.

(56) References Cited

U.S. PATENT DOCUMENTS

| 5,858,995 | A * | 1/1999 | Kawai et al. ................... 514/100 |
| 5,874,427 | A * | 2/1999 | Filla et al. ................. 514/214.01 |
| 6,878,714 | B2 * | 4/2005 | Askew ................. C07D 213/82 514/256 |
| 6,995,162 | B2 * | 2/2006 | Chen .................... C07D 213/82 514/256 |
| 7,101,868 | B2 * | 9/2006 | Elbaum ................. C04B 35/632 514/183 |
| 7,102,009 | B2 * | 9/2006 | Patel ...................... A61K 31/00 544/253 |
| 7,105,682 | B2 * | 9/2006 | Chen ...................... A61K 31/00 544/253 |
| 7,507,748 | B2 * | 3/2009 | Yuan .................... C07D 217/02 514/310 |
| 2003/0099936 | A1 | 5/2003 | Sugden et al. ..................... 435/5 |
| 2005/0074751 | A1 | 4/2005 | Harley et al. ..................... 435/5 |
| 2006/0293332 | A1 | 12/2006 | Grant et al. ................... 514/249 |
| 2010/0093819 | A1 | 4/2010 | Morita et al. ................. 514/406 |

FOREIGN PATENT DOCUMENTS

| EP | 0875513 A1 | 11/1998 |
| EP | 1820795 A1 | 8/2007 |
| EP | 2589592 A1 | 5/2013 |
| WO | WO 9529907 A1 * | 11/1995 |
| WO | WO 9846570 A1 * | 10/1998 |
| WO | WO00/34238 | 6/2000 |
| WO | WO02055501 A2 * | 7/2002 ........... C07D 213/81 |
| WO | WO02/066470 A1 | 8/2002 |
| WO | WO02/083654 A1 | 10/2002 |
| WO | WO 2008/076077 A1 | 6/2008 |
| WO | WO2008/118379 A2 | 10/2008 |
| WO | WO2009/052065 A1 | 4/2009 |
| WO | WO2010/074244 A1 | 1/2010 |
| WO | WO 2010123139 A1 * | 10/2010 |

OTHER PUBLICATIONS

Ambinder et al. "Definition of the Sequence Requirements for Binding of the EBNA-1 Protein to its Palindromic Target Sites in Epstein-Barr Virus DNA" Journal of Virology 1990 64(5):2369-2379.

Bochkarev et al. "Crystal Structure of the DNA-Binding Domain of the Epstein-Barr Virus Origin-Binding Protein EBNA1" Cell 1995 83:39-46.

Bochkarev et al. "Crystal Structure of the DNA-Binding Domain of the Epstein-Barr Virus Origin-Binding Protein, EBNA1, Bound to DNA" Cell 1996 84:791-800.

Bowser et al. "Novel Anti-Infection Agents: Small-Molecule Inhibitors of Bacterial Transcription Factors" Bioorganic & Medicinal Chemistry Letters 2007 17:5652-5655.

(Continued)

*Primary Examiner* — Nyeemah A Grazier

(74) *Attorney, Agent, or Firm* — Licata & Tyrrell P.C.

(57) ABSTRACT

The present invention embraces compounds that modulate the activity of Epstein-Barr Nuclear Antigen 1 (BBNA1) protein and use thereof in methods for treating latent Epstein-Barr virus infection. R7 is a substituted or unsubstituted phenyl, pyridyl, or pyrimidinyl group. A pharmaceutical composition comprising a compound of the invention in admixture with a pharmaceutically acceptable carrier is also provide as are methods for modulating the activity of Epstein-Barr Nuclear Antigen 1 (EBNA1) protein and treating a latent EpsteinBarr virus infection with a composition of the present invention.

3 Claims, No Drawings

(56) References Cited

OTHER PUBLICATIONS

Garber et al. "Latency-Associated Nuclear Antigen (LANA) Cooperatively Binds to Two Sites within the Terminal Repeat, and Both Sites Contribute to the Ability of LANA to Suppress Transcription and to Facilitate DNA Replication" The Journal of Biological Chemistry 2002 277:27401-27411.
Humme et al. "The EBV Nuclear Antigen 1 (EBNA1) Enhances B Cell Immortalization Several Thousandfold" Proceedings of the National Academy of Sciences 2003 100(19):10989-10994.
Kennedy et al. "Epstein-Barr Virus Provides a Survival Factor to Burkitt's Lymphomas" Proceedings of the National Academy of Sciences 2003 100(24):14269-14274.
Kieff, E.D. and Rickinson, A.B. "Epstein-Barr Virus and its Replication" *Fields Virology* 5th edition Philadelphia, PA: Wolters Kluwer/Lippincott Williams and Wilkins, 2007 pp. 2603-2654.
Kiessling et al. "Selective Inhibition of c-Myc/Max Dimerization and DNA Binding by Small Molecules" Chemistry & Biology 2006 13:745-751.
Leight, E.R. and Sugden, B. "EBNA-1: A Protein Pivotal to Latent Infection by Epstein-Barr Virus" Reviews in Medical Virology 2000 10:83-100.
Li et al. "Discovery of Selective Inhibitors Against EBNA1 via High Throughput in Silico Virtual Screening" PLoS One 2010 5(4):e10126.
Mao et al. "A New Small Molecule Inhibitor of Estrogen Receptor α Binding to Estrogen Response Elements Blocks Estrogen-Dependent Growth of Cancer Cells" The Journal of Biological Chemistry 2008 283:12819-12830.
Rawlins et al. "Sequence-Specific DNA Binding of the Epstein-Barr Virus Nuclear Antigen (EBNA-1) to Clustered Sites in the Plasmid Maintenance Region" Cell 1985 42:859-868.
Rickinson, A.B. and Kieff, E.D. "Epstein-Barr Virus" *Fields Virology* 5th edition Philadelphia, PA: Wolters Kluwer/Lippincott Williams and Wilkins, 2007 pp. 2656-2700.
Rishi et al. "A High-Throughput Fluorescence-Anisotropy Screen that Identifies Small Molecule Inhibitors of the DNA Binding of B-ZIP Transcription Factors" Analytical Biochemistry 2005 340:259-271.
Siddiquee et al. "Selective Chemical Probe Inhibitor of Stat3, Identified through Structure-Based Virtual Screening, Induces Antitumor Activity" Proceedings of the National Academy of Sciences 2007 104(18):7391-7396.
Thompson et al. "Development of a High-Throughput Screen for Inhibitors of Epstein-Barr Virus EBNA1" Journal of Biomolecular Screening 2010 15(9):1107-1115.
Thorley-Lawson, D.A. and Gross, A. "Persistence of the Epstein-Barr Virus and the Origins of Associated Lymphomas" The New England Journal of Medicine 2004 350:1328-1337.
Vangrevelinghe et al. "Discovery of a Potent and Selective Protein Kinase CK2 Inhibitor by High-Throughput Docking" Journal of Medicinal Chemistry 2003 46:2656-2662.
Wang et al. "Essential Elements of a Licensed, Mammalian Plasmid Origin of DNA Synthesis" Molecular and Cellular Biology 2006 26(3):1124-1134.
Yates et al. "Stable Replication of Plasmids Derived from Epstein-Barr Virus in Various Mammalian Cells" Nature 1985 313:812-815.
Yin, Q. and Flemington, E.K. "SiRNAs Against the Epstein Barr Virus Latency Replication Factor, EBNA1, Inhibit its Function and Growth of EBV-Dependent Tumor Cells" Virology 2006 346:385-393.
Young, L.S. and Rickinson, A.B. "Epstein-Barr Virus: 40 Years On" Nature Reviews Cancer 2004 4:757-768.
International Search Report from PCT/US2012/038938, Aug. 24, 2012, PCT.
Erlenmeyer et al. "Zur Kenntnis des 5-Aminocumarons" Helvetic Chimica Acta, Verlag Helvetica Chimica Acta, CH, 1948 31:75-77 (English language summary of Erlenmyer et al.).
Extended Search Report from EP12789638, Nov. 4, 2014, EP.
International Preliminary Report on Patentability from PCT/US2012/038938, Dec. 5, 2013, PCT.

\* cited by examiner

SEQUENCE LISTING

<160> NUMBER OF SEQ ID NOS: 2

<210> SEQ ID NO 1
<211> LENGTH: 641
<212> TYPE: PRT
<213> ORGANISM: Human herpesvirus 4

<400> SEQUENCE: 1

Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Gly Ser Gly Pro Gln
            20                  25                  30

Arg Arg Gly Gly Asp Asn His Gly Arg Gly Arg Gly Arg Gly Arg Gly
        35                  40                  45

Arg Gly Gly Arg Pro Gly Ala Pro Gly Gly Ser Gly Ser Gly Pro
    50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                85                  90                  95

Gly Ala Gly Ala Gly Gly Ala Gly Ala Gly Gly Ala Gly Ala Gly
            100                 105                 110

Gly Gly Ala Gly Gly Ala Gly Gly Ala Gly Gly Ala Gly Gly Ala Gly Gly
        115                 120                 125

Gly Ala Gly Ala Gly Gly Ala Gly Gly Ala Gly Gly Ala Gly Ala
    130                 135                 140

Gly Gly Gly Ala Gly Ala Gly Gly Ala Gly Gly Ala Gly Ala Gly
145                 150                 155                 160

Gly Gly Ala Gly Gly Ala Gly Gly Ala Gly Ala Gly Gly Ala Gly
                165                 170                 175

Ala Gly Gly Gly Ala Gly Gly Ala Gly Ala Gly Gly Ala Gly Gly
            180                 185                 190

Ala Gly Gly Ala Gly Ala Gly Gly Ala Gly Ala Gly Gly Ala Gly
        195                 200                 205

Gly Ala Gly Gly Ala Gly Ala Gly Gly Ala Gly Ala Gly Gly Ala
    210                 215                 220

Gly Gly Ala Gly Gly Ala Gly Ala Gly Gly Ala Gly Ala Gly Gly Ala
225                 230                 235                 240

Gly Ala Gly Gly Ala Gly Ala Gly Gly Ala Gly Ala Gly Gly Ala Gly
                245                 250                 255

Gly Ala Gly Gly Ala Gly Ala Gly Gly Ala Gly Ala Gly Gly Ala Gly
            260                 265                 270

Gly Gly Ala Gly Gly Ala Gly Ala Gly Gly Ala Gly Gly Ala Gly

```
                275                 280                 285
Ala Gly Gly Ala Gly Gly Ala Gly Ala Gly Gly Ala Gly Gly Ala Gly
        290                 295                 300
Ala Gly Gly Ala Gly Gly Ala Gly Ala Gly Gly Ala Gly Gly Ala Gly
305                 310                 315                 320
Gly Ala Gly Ala Gly Gly Gly Arg Gly Arg Gly Gly Ser Gly Gly
                325                 330                 335
Arg Gly Arg Gly Gly Ser Gly Gly Arg Gly Arg Gly Gly Ser Gly Gly
            340                 345                 350
Arg Arg Gly Arg Gly Arg Glu Arg Ala Arg Gly Gly Ser Arg Glu Arg
            355                 360                 365
Ala Arg Gly Arg Gly Arg Gly Arg Gly Glu Lys Arg Pro Arg Ser Pro
        370                 375                 380
Ser Ser Gln Ser Ser Ser Gly Ser Pro Pro Arg Arg Pro Pro Pro
385                 390                 395                 400
Gly Arg Arg Pro Phe Phe His Pro Val Gly Glu Ala Asp Tyr Phe Glu
                405                 410                 415
Tyr His Gln Glu Gly Gly Pro Asp Gly Glu Pro Asp Val Pro Pro Gly
            420                 425                 430
Ala Ile Glu Gln Gly Pro Ala Asp Asp Pro Gly Glu Gly Pro Ser Thr
            435                 440                 445
Gly Pro Arg Gly Gln Gly Asp Gly Arg Arg Lys Lys Gly Gly Trp
        450                 455                 460
Phe Gly Lys His Arg Gly Gln Gly Gly Ser Asn Pro Lys Phe Glu Asn
465                 470                 475                 480
Ile Ala Glu Gly Leu Arg Ala Leu Leu Ala Arg Ser His Val Glu Arg
                485                 490                 495
Thr Thr Asp Glu Gly Thr Trp Val Ala Gly Val Phe Val Tyr Gly Gly
            500                 505                 510
Ser Lys Thr Ser Leu Tyr Asn Leu Arg Arg Gly Thr Ala Leu Ala Ile
            515                 520                 525
Pro Gln Cys Arg Leu Thr Pro Leu Ser Arg Leu Pro Phe Gly Met Ala
        530                 535                 540
Pro Gly Pro Gly Pro Gln Pro Gly Pro Leu Arg Glu Ser Ile Val Cys
545                 550                 555                 560
Tyr Phe Met Val Phe Leu Gln Thr His Ile Phe Ala Glu Val Leu Lys
                565                 570                 575
Asp Ala Ile Lys Asp Leu Val Met Thr Lys Pro Ala Pro Thr Cys Asn
            580                 585                 590
Ile Arg Val Thr Val Cys Ser Phe Asp Asp Gly Val Asp Leu Pro Pro
            595                 600                 605
Trp Phe Pro Pro Met Val Glu Gly Ala Ala Glu Gly Asp Asp Gly
        610                 615                 620
Asp Asp Gly Asp Glu Gly Gly Asp Gly Asp Glu Gly Glu Gly Gln
625                 630                 635                 640
Glu

<210> SEQ ID NO 2
<211> LENGTH: 36
<212> TYPE: DNA
<213> ORGANISM: Artificial sequence
```

```
<220> FEATURE:
<223> OTHER INFORMATION: Synthetic oligonucleotide

<400> SEQUENCE: 2
gggtagcata tgctatctag atagcatatg ctaccc                    36
```

COMPOSITIONS AND METHODS FOR MODULATING THE ACTIVITY OF EPSTEIN-BARR NUCLEAR ANTIGEN 1

This application is the national stage under 35 U.S.C. §371 of PCT International Application No. PCT/US2012/038938, filed May 22, 2012, which claims priority from U.S. 61/489,293, filed May 24, 2011, the contents of which are incorporated herein by reference in their entireties.

This invention was made with government support under contract numbers R21 3R21NS063906 and R43 1R43AI079928 awarded by the National Institutes of Health. The government has certain rights in the invention.

BACKGROUND OF THE INVENTION

Epstein-Barr virus (EBV) is a carcinogenic cofactor for several lymphoid and epithelial cell malignancies (Kieff (2007) *Epstein-Barr Virus and its Replication*, 5th ed. Wolters Kluwer Health/Lippincott Williams & Wilkins, Philadelphia; Rickinson & Kieff (2007) *Epstein-Barr Virus*, 5th ed. Wolters Kluwer Health/Lippincott Williams & Wilkins, Philadelphia; Young & Rickinson (2004) *Nat. Rev. Cancer* 4:757-68). EBV is associated with the majority of endemic forms of Burkitt's lymphoma and nasopharyngeal carcinomas (NPC). EBV is also found in ~50% of all Hodgkin's disease tumor biopsies, some forms of gastric carcinoma, thyroid tumors, NK/T cell lymphoma, and the majority of immunosuppression-associated non-Hodgkin's lymphomas and lymphoproliferative disease. Most EBV associated tumors harbor the latent viral genome as a multicopy episome in the nucleus of the transformed cells. During latent infection, EBV does not produce progeny virions, but does express a limited set of viral gene products that promote host-cell survival and proliferation. In proliferating cells, the maintenance of the latent viral genome depends on the functions of the Epstein-Barr Nuclear Antigen 1 (EBNA1) protein (Leight & Sugden (2000) *Rev. Med. Virol.* 10:83-100). EBNA1 is expressed in all types of EBV latent infection found in proliferating cells and tumors. EBNA1 is essential for the immortalization of primary B lymphocytes by EBV infection (Humme, et al. (2003) *Proc. Natl. Acad. Sci. USA* 100:10989-94), and its inhibition by siRNA depletion or by ectopic expression of dominant negative mutants causes infected cells death (Kennedy, et al. (2003) *Proc. Natl. Acad. Sci. USA* 100:14269-14274; Yin & Flemington (2006) *Virology* 346:385-93).

EBNA1 is a candidate for targeting inhibition of EBV latent infection. EBNA1 is consistently expressed in most, if not all, EBV-associated malignancies (Thorley-Lawson & Gross (2004) *N. Engl. J. Med.* 350:1328-37). EBNA1 is essential for viral genome maintenance and for infected-cell survival (Kennedy, et al. (2003) supra; Yin & Flemington (2006) supra). Most importantly, EBNA1 is a viral-encoded protein that has well-defined biochemical and structural properties. EBNA1 is composed of two major functional domains, a carboxy-terminal DNA binding domain, and an amino-terminal chromosome tethering domain (Leight & Sugden (2000) supra; Wang, et al. (2006) *Mol. Cell. Biol.* 26:1124-34). The DNA binding domain is essential for interaction with the viral origin of plasmid replication (OriP) (Yates, et al. (1985) *Nature* 313:812-815). OriP is composed of a series of 30 bp repeats to which EBNA1 binds an 18 bp palindromic-sequence as a homodimer (Ambinder, et al. (1990) *J. Virol.* 64:2369-79; Rawlins, et al. (1985) *Cell* 42:859-68). The DNA binding and dimerization interface have been solved by high resolution X-ray crystallography in the apo- and DNA-bound forms (Bochkarev, et al. (1996) *Cell* 84:791-800; Bochkarev, et al. (1995) *Cell* 83:39-46). While there are no known cellular homologues of EBNA1, the three dimensional structure of EBNA1 resembles the overall structure of human papillomavirus (HPV) E2 protein, which has an analogous function to EBNA1 at the HPV origin of DNA replication (Bochkarev, at al. (1995) supra). Protein structure prediction programs suggest that EBNA1 and E2 share structural folds similar to the Kaposi's Sarcoma Associated herpesvirus (KSHV) LANA protein, which shares many functional properties with EBNA1, including DNA binding and episome maintenance of KSHV oriP (Garber, et al. (2002) *J. Biol. Chem.* 277:27401-11). These observations suggest that EBNA1 is a member of a family of viral origin binding proteins that have no apparent orthologue in the human genome, and therefore may represent attractive targets for inhibitors of viral latent replication and persistence.

Identification of small molecules that specifically inhibit protein-DNA binding activity has had some success (Bowser, et al. (2007) *Bioorg. Med. Chem. Lett.* 17:5652-5; Kiessling, et al. (2006) *Chem. Biol.* 13:745-51; Mao, et al. (2008) *J. Biol. Chem.* 283:12819-30; Rishi, at al. (2005) *Anal. Biochem.* 340:259-71). Because of the cost-inefficient and time-consuming process of conventional drug discovery over the past decade, high throughput virtual screening (HTVS) has emerged as an attractive and complementary approach to traditional HTS. HTVS typically depends on the availability of a high-resolution crystal structure of the protein target as a template for computational screening. Over the years, HTVS has been applied to the successful identifications of biologically active molecules against targets such as HIV-1 protease, thymidylate, influenza hemagglutinin, and parasitic proteases (Siddiquee, et al. (2007) *Proc. Natl. Acad. Sci. USA* 104:7391-7396; Vangrevelinghe, et al. (2003) J. Med. Chem. 46:2656-2662).

SUMMARY OF THE INVENTION

The present invention features a compound of Formula I, II or III.

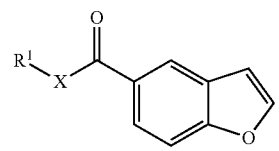

Formula I

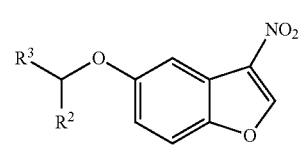

Formula II

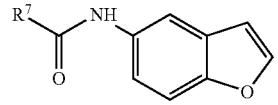

Formula III wherein
X is O or NH;
R$^1$ is a substituted or unsubstituted phenyl, pyridyl or thiazole group.
R$^2$ is =O or 2H;
R$^3$ is CR$^4$, a substituted or unsubstituted pyridyl group, a pyrimidinyl group, a phenylmorpholine group; an oxazole group, or

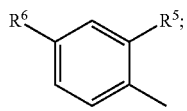

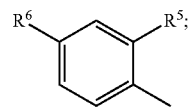

R⁴ is a substituted or unsubstituted phenyl group;

R⁵ and R⁶ are independently a halogen group, a substituted or unsubstituted lower alkyl group, or substituted or unsubstituted methoxy group, with the proviso that when $R^2$ is =O and R⁵ is H, R⁶ is not Cl, C(CH₃)₃, or CF₃; and R⁷ is a substituted or unsubstituted phenyl, pyridyl, or pyrimidinyl group. A pharmaceutical composition comprising a compound of the invention in admixture with a pharmaceutically acceptable carrier is also provide as are methods for modulating the activity of Epstein-Barr Nuclear Antigen 1 (EBNA1) protein and treating a latent Epstein-Barr virus infection with a composition of the present invention.

DETAILED DESCRIPTION OF THE INVENTION

Fluorescence polarization (FP)-based high throughput screening and electrophoresis mobility shift assays (EMSA) were conducted to identify small molecule inhibitors of Epstein-Barr Nuclear Antigen 1 (EBNA1). Compounds identified in these assays were found to be highly selective inhibitors of EBNA1. These compounds, as well as analogs and derivatives thereof, serve as new EBNA1 inhibitors for use as therapeutic agents against EBV. Accordingly, the present invention features the compounds identified herein and their use in treating a latent Epstein-Barr virus infection.

The compounds of the present invention were found to share a common benzofuran structure. More specifically, the compounds of the invention had the structures of Formula I, Formula II and Formula III.

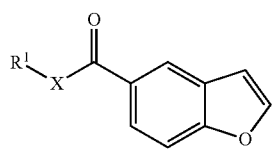

Formula I

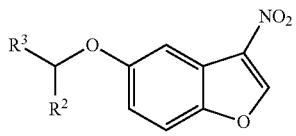

Formula II

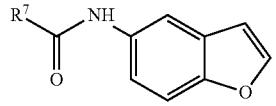

Formula III wherein X is O or NH;

R¹ is a substituted or unsubstituted phenyl, pyridyl or thiazole group.

$R^2$ is =O or 2H;

R³ is CR⁴, a substituted or unsubstituted pyridyl group, a pyrimidinyl group, a phenylmorpholine group; an oxazole group, or R⁴ is a substituted or unsubstituted phenyl group;

R⁵ and R⁶ are independently a halogen group, a substituted or unsubstituted lower alkyl group, or substituted or unsubstituted methoxy group, with the proviso that when $R^2$ is =O and R⁵ is H, R⁶ is not Cl, C(CH₃)₃, or CF₃; and R⁷ is a substituted or unsubstituted phenyl, pyridyl, or pyrimidinyl group.

"Lower alkyl" is intended to mean a branched or unbranched saturated monovalent hydrocarbon radical containing 1 to 6 carbon atoms, such as methyl, ethyl, propyl, isopropyl, tert-butyl, butyl, n-hexyl and the like.

Exemplary substituent groups include, but are not limited to, halogen (i.e., fluorine, chlorine, bromine and iodine), lower alkyl, ethoxy, methoxy, hydroxyl, amine, amide, nitro, nitroso, aldehyde, carboxyl, sulfhydryl, and carbonothioyl.

Exemplary compounds of Formula I, Formula II and Formula III are presented in Table 2. Such compounds can be prepared as pharmaceutical compositions, pharmaceutically acceptable derivatives, or pharmaceutically acceptable salts and be provided alone or in combination in the form of a kit with unit doses of the subject compounds. In such kits, in addition to the containers containing the unit doses will be an informational package insert describing the use and attendant benefits of using the compound(s).

A "pharmaceutically acceptable derivative" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

In addition to the compounds specifically disclosed herein, the present invention also pertains to analogs and derivatives of said compounds that modulate EBNA1 activity. Broadly, the EBNA1 three-dimensional crystal structure in combination with the structure of the instant compounds can be used to design or screen for a test compound with EBNA1 inhibitory activity; and the compound designed or screened for can be tested for its ability to modulate the activity of EBNA1. In certain embodiments, the screening is carried out using various in silico, in vitro and/or in vivo assays based on detecting interactions between the DNA binding domain or residues of the DNA binding domain of EBNA1 and a test compound.

In the context of the present invention, EBNA1 refers to the Epstein-Barr Nuclear Antigen 1 protein. EBNA1 is described, e.g., in GENBANK Accession No. YP_401677, and set forth herein in SEQ ID NO:1. Full-length EBNA1 protein can be used in accordance with this invention or alternatively, the DNA binding domain of EBNA1 can be used (i.e., amino acid residues 454 to 607). For the purposes of the present invention, reference to EBNA1 also includes synthetic variants of EBNA1, as well as fragments of EBNA1. Synthetic variants include those which have at least 80%, preferably at least 90%, homology to EBNA1 disclosed herein and possess the ability to bind DNA. More preferably, such variants correspond to the sequence of EBNA1 provided herein, but have one or more, e.g., from 1 to 10, or from 1 to 5 substitutions, deletions or insertions of amino acids. Fragments of EBNA1 and variants thereof are preferably between 100 and 500 amino acid residues in length or between 150 and 300 amino acids in length. An exemplary fragment includes the approximately 150 amino acid residues encompassing the DNA binding domain of EBNA1.

In accordance with the present invention, molecular design techniques can be employed to design, identify and synthesize analogs and derivatives, including inhibitory and stimulatory compounds, capable of binding to one or more amino acids of the DNA binding pocket of EBNA1. The structure of the DNA binding pocket of EBNA1 can be used in conjunction with computer modeling using a docking program such as GRAM, DOCK, HOOK or AUTODOCK (Dunbrack, et al. (1997) *Folding & Design* 2:27-42) to identify potential modulators of EBNA1 protein. This procedure can include computer fitting of compounds to the DNA binding pocket of EBNA1 to, e.g., ascertain how well the shape and the chemical structure of the compound will complement the DNA binding domain; or to compare the compound with the binding of an inhibitor disclosed herein. Computer programs can also be employed to estimate the attraction, repulsion and stearic hindrance of the EBNA1 protein and effector compound. Generally, the tighter the fit, the lower the stearic hindrances, the greater the attractive forces, and the greater the specificity, which are important features for a specific effector compound which is more likely to interact with the EBNA1 protein rather than other classes of proteins.

A chemical-probe approach can be alternatively or additionally be employed in the design of EBNA1 modulators or effectors. For example, Goodford ((1985) *J. Med. Chem.* 28:849) describes several commercial software packages, such as GRID (Molecular Discovery Ltd., Oxford, UK), which can be used to probe the EBNA1 DNA binding domain with different chemical probes, e.g., water, a methyl group, an amine nitrogen, a carboxyl oxygen, and a hydroxyl. Favored sites for interaction between the EBNA1 DNA binding domain and each probe are thus determined, and from the resulting three-dimensional pattern a putative complementary molecule can be generated.

Analogs and derivatives of the compounds of the present invention can also be designed by visually inspecting the three-dimensional structure of the EBNA1 DNA binding domain to determine more effective inhibitors or activators. This type of modeling is generally referred to as "manual" drug design. Manual drug design can employ visual inspection and analysis using a graphics visualization program such as "O" (Jones, et al. (1991) *Acta Crystallographica Section A* A47:110-119). Initially effector compounds are selected by manual drug design. The structural analog thus designed can then be modified by computer modeling programs to better define the most likely effective candidates. Reduction of the number of potential candidates is useful as it may not be possible to synthesize and screen a countless number of compound variations that may have some similarity to known inhibitory molecules. Such analysis has been shown effective in the development of HIV protease inhibitors (Lam, et al. (1994) *Science* 263:380-384; Wlodawer, et al. (1993) *Ann. Rev. Biochem.* 62:543-585; Appelt (1993) *Perspectives in Drug Discovery and Design* 1:23-48; Erickson (1993) *Perspectives in Drug Discovery and Design* 1:109-128).

Programs suitable for searching three-dimensional databases include MACCS-3D and ISIS/3D (Molecular Design Ltd, San Leandro, Calif.), ChemDBS-3D (Chemical Design Ltd., Oxford, UK), and Sybyl/3 DB Unity (Tripos Associates, St Louis, Mo.). Programs suitable for compound selection and design include, e.g., DISCO (Abbott Laboratories, Abbott Park, Ill.), Catalyst (Bio-CAD Corp., Mountain View, Calif.), and ChemDBS-3D (Chemical Design Ltd., Oxford, UK).

Analogs and derivatives of the compounds of the present invention can bind to all or a portion of the DNA binding domain of EBNA1 and may be more potent, more specific, less toxic and more effective than the instant compounds. The designed compounds can also be less potent but have a longer half-life in vivo and/or in vitro and therefore be more effective at modulating EBNA1 activity in vivo and/or in vitro for prolonged periods of time. Such designed modulators are useful to activate EBNA1 or inhibit EBNA1 activity to, e.g., prevent tumor formation.

The present invention also provides the use of molecular design techniques to computationally screen small molecule databases for chemical entities or compounds that can bind to EBNA1 in a manner analogous to its natural substrates and/or compounds disclosed herein. Such computational screening can identify various groups which interact with one or more amino acid residues of the DNA binding domain and can be employed to synthesize modulators of the present invention.

In vitro (i.e., in solution) screening assays are also embraced by the present invention. For example, such assays include combining EBNA1 or the EBNA1 DNA binding domain (e.g., as disclosed herein), with or without substrates (e.g., a DNA probe) in solution and determining whether an analog or derivative can block or enhance EBNA1 DNA binding activity. In this respect, in vitro screening assays can be carried out to monitor DNA binding in the presence or absence of an analog or derivative. In accordance with this aspect of the invention, the present invention embraces the use of a FP-based assay and/or EMSA to demonstrate binding of an analog or derivative to the DNA binding domain of EBNA1. Such assays are routinely practiced in the art and disclosed in more detail herein.

After designing or screening for an analog or derivative, the analog or derivative is subsequently tested for its ability to modulate the activity of EBNA1 in vivo. This can be carried out using conventional assays such as the cell-based reporter assay disclosed herein or by determining EBV genome copy number maintenance.

To further evaluate the efficacy of a compound, analog or derivative of the invention, one of skill will appreciate that a model system of any particular disease or disorder involving latent EBV infection can be utilized to evaluate the adsorption, distribution, metabolism and excretion of a compound as well as its potential toxicity in acute, sub-chronic and chronic studies. For example, the effector or modulatory compound can be tested in the model disclosed in Example 2, the EBV model using beige/nude/xid mice carrying human lymphoid xenografts (Dosch, et al. (1991) *Internation. Immunol.* 3:731-35) or SCID mice engrafted with human lymphocytes (Rowe, et al. (1991) *J. Exp. Med.* 173:147-158). Ultimately, the safety and efficacy of compounds of the invention are evaluated in human clinical trials.

Compounds of this invention have a variety of uses. EBNA1 protein is expressed in all EBV-associated tumors, where it is indispensable for viral replication, genome maintenance and viral gene expression. EBNA1's transcription factor-like functions also extend to influencing the expression of cellular genes involved in pathways commonly dysregulated during oncogenesis. Therefore, in one embodiment inhibitors of EBNA1 DNA binding activity inhibit viral replication by disruption of EBNA1 DNA binding. In many cases, inhibition of viral replication equates with inhibition of tumor formation. Therefore, inhibitors of EBNA1 DNA binding activity will be effective therapeutic agents for treatment of human diseases or conditions caused by EBV latent infection, in particular EBV-associated tumors. In addition to the regulation of viral genes, EBNA1 has been shown to regulate host cell gene expression. For example, EBNA1 has been shown to induce the expression of CD25, RAG1, RAG2 and CCL20 in B-cells (Baumforth, et al. (2008) *Am. J. Pathol.* 173:195-204; Kube, et al. (1999) *J. Virol.* 73:1630-1636; Srinivas & Sixbey (1995) *J. Virol.* 69:8155-8158), and the differential regulation of cellular genes involved in translation, transcription and cell signaling in epithelial cells (O'Neil, et al. (2008) *J. Gen. Virol.* 89:2833-2842; Wood, et al. (2007) *Oncogene* 26:4135-4147). Furthermore, EBNA1 enhances STAT1 expression which sensitizes cells to interferon-induced STAT1 activation, modulates signaling in the TGFβ1 pathway, and increases AP-1 activity resulting in the enhancement of host cell mechanisms involved in angiogenesis and metastasis (O'Neil, et al. (2008) supra; Wood, et al. (2007) supra). Accordingly, compounds that activate EBNA1 are of use in inducing the lytic cycle of EBV to study pathogenesis and analyze the effect of EBNA1 on host cell gene expression. In general, the molecules of the invention can be used whenever it is desired to increase or decrease EBNA1 activity in a cell or organism.

Therefore, the compounds, analogs and derivatives of the present invention find application in a method for modulating (i.e., blocking or inhibiting, or enhancing or activating) EBNA1. Such a method involves contacting EBNA1 either in vitro or in vivo with an effective amount of a compound, analog or derivative of the invention so that the activity of EBNA1 is modulated. An effective amount of an effector or modulatory compound is an amount which reduces or increases the activity of the EBNA1 by at least 30%, 40%, 50%, 60%, 70%, 80%, 90% or 100% when compared to EBNA1 not contacted with the compound. Such activity can be monitored by reporter-based assays for detecting activity of the EBNA1 or in competitive binding assays with a DNA substrate. Compounds particularly embraced by the invention are provided herein in the Examples.

One of skill in the art can appreciate that modulating the activity of EBNA1 can be useful in selectively analyzing EBNA1 signaling events in model systems as well as in preventing or treating diseases, conditions, and disorders involving EBNA1 latent infection. The selection of the compound for use in preventing or treating a particular disease or disorder will be dependent upon the particular disease or disorder. For example, EBNA1 is involved in cancer and therefore a compound which inhibits EBNA1 will be useful in the prevention or treatment of cancer including, but not limited to Burkitt's lymphoma, nasopharyngeal carcinoma, Hodgkin's lymphoma, post-transplant lymphoproliferative disease, some forms of gastric carcinoma, thyroid tumors, NK/T cell lymphoma, and immunosuppression-associated non-Hodgkin's lymphomas. Moreover, EBV has been suspected to have a role in the pathogenesis of chronic fatigue syndrome (Lerner, et al. (2004) *In Vivo* 18:101-6), such that inhibition of EBNA1 may be of use in treating this condition as well.

Accordingly, the present invention also provides a method for preventing or treating a latent Epstein-Barr virus infection. Such treatment involves administering to a subject in need of treatment a pharmaceutical composition containing an effective amount of an EBNA1 inhibitory compound disclosed herein (see, e.g., Table 2). In most cases this will be a human being, but treatment of agricultural animals, e.g., livestock and poultry, and companion animals, e.g., dogs, cats and horses, is expressly covered herein.

As used herein the terms "treating" and "treatment" refer to any and all uses which remedy a condition or symptoms, prevent the establishment of a condition or disease, or otherwise prevent, hinder, retard, or reverse the progression of a condition or disease or other undesirable symptoms.

As used herein the term "effective amount" includes within its meaning a non-toxic but sufficient amount of an agent or compound to provide the desired effect. The exact amount required will vary from subject to subject depending on factors such as the species being treated, the age and general condition of the subject, the severity of the condition being treated, the particular agent being administered and the mode of administration and so forth. In this respect, for any given case, an appropriate "effective amount" may be determined by one of ordinary skill in the art using only routine experimentation.

Pharmaceutical compositions containing a compound of the invention can be in the form of pharmaceutically acceptable salts and complexes and can be provided in a pharmaceutically acceptable carrier and at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically-acceptable carrier, composition or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the subject being treated.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and anti-oxidants can also be present in the compositions.

The compositions of the present invention can be administered parenterally (for example, by intravenous, intraperitoneal, subcutaneous or intramuscular injection), topically (including buccal and sublingual), orally, intranasally, intravaginally, or rectally according to standard medical practices.

The selected dosage level will depend upon a variety of factors including the activity of the particular compound of the present invention employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of a compound at levels lower than that required in order to achieve the desired therapeutic effect and gradually increase the dosage until the desired effect is achieved. This is considered to be within the skill of the artisan and one can review the existing literature on a specific compound or similar compounds to determine optimal dosing.

In addition to the treatment of EBV latent infection, it is envisioned that the compounds disclosed herein will be equally suitable for inhibition of other viruses with similar DNA binding domains. For example, EBNA1 resembles the overall structure of human papillomavirus (HPV) E2 protein, which has an analogous function to EBNA1 at the HPV origin of DNA replication (Bochkarev, et al. (1995) supra). Protein structure prediction programs indicate that EBNA1, and E2 share structural folds similar to the Kaposi's Sarcoma Associated herpesvirus (KSHV) LANA protein, which shares many functional properties with EBNA1, including DNA binding and episome maintenance of KSHV oriP (Garber, et al. (2002) supra). Therefore, effectors identified in accordance with the method disclosed herein may also be useful in modulating the activity of LANA and E2 proteins, as well as in the treatment of diseases associated with KSHV and HPV.

The invention is described in greater detail by the following non-limiting examples.

Example 1

Parallel Synthesis of Compounds

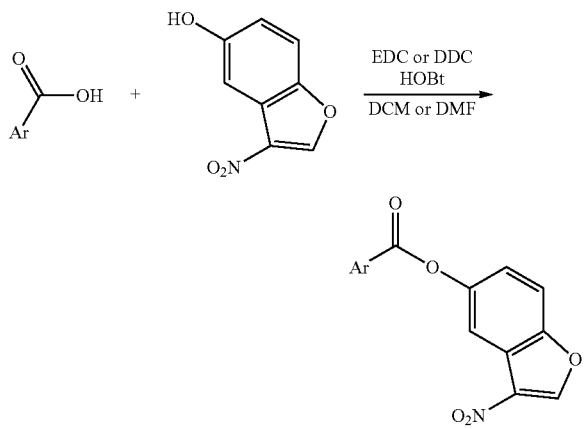

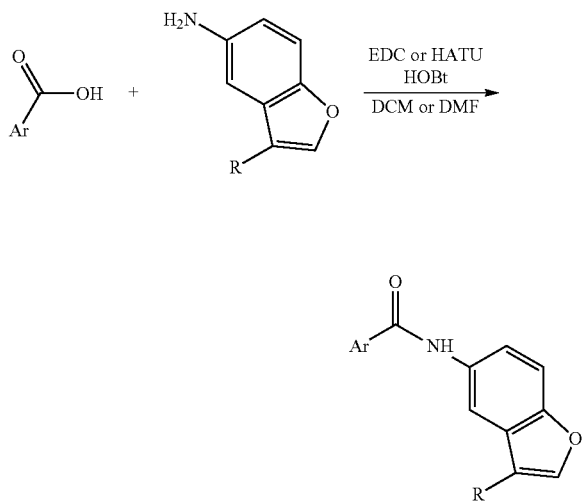

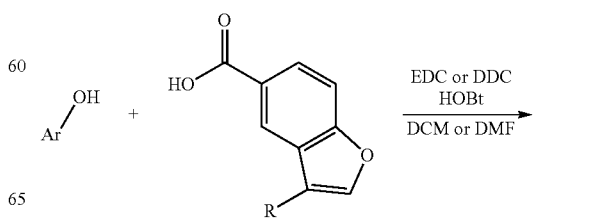

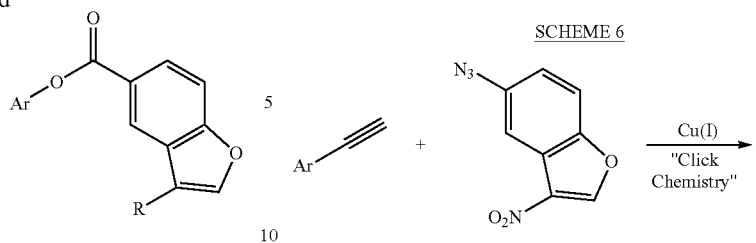
SCHEME 4
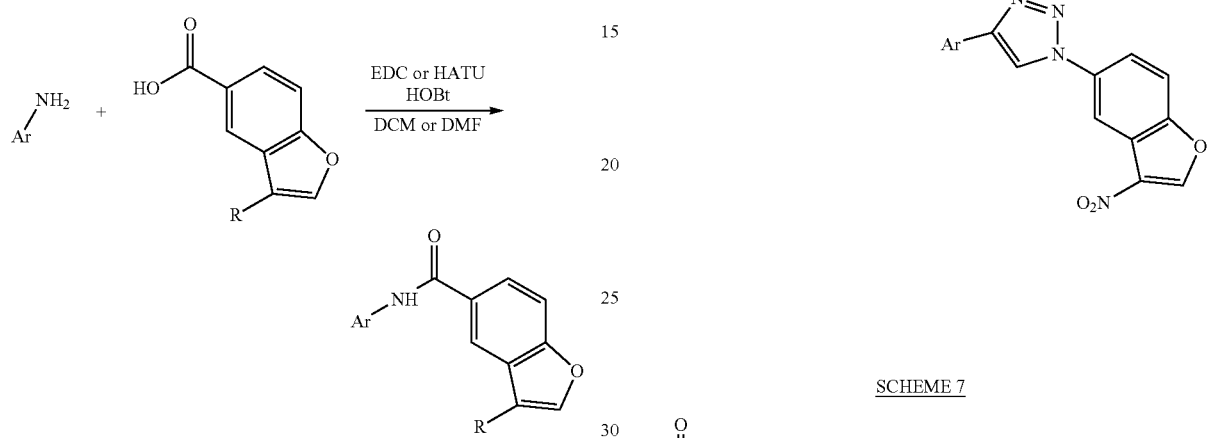
SCHEME 5
SCHEME 6
SCHEME 7
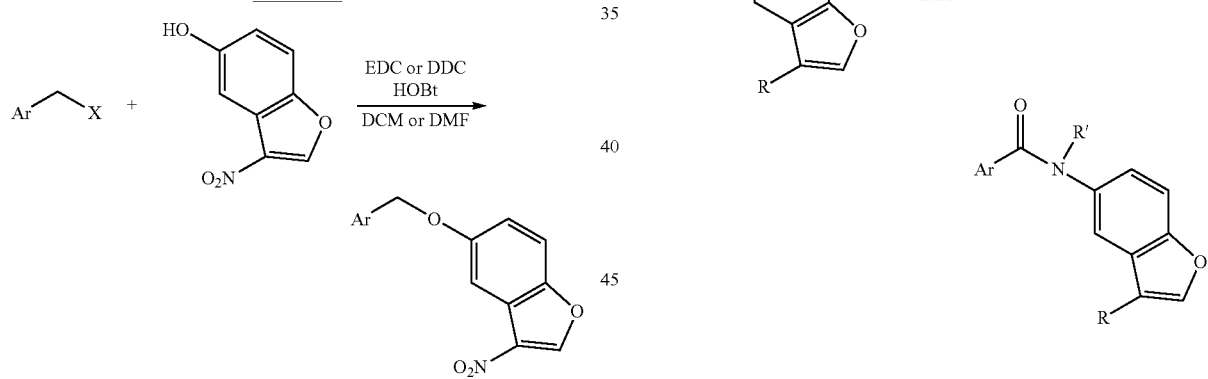
Substituents of the compounds synthesized according to Schemes 1-7 are listed in Table 1.
TABLE 1
| R | | | R'—X |
|---|---|---|---|
| H₃C-C(CH₃)₂-C₆H₄- (4-tert-butylphenyl) | 2,4-dichlorophenyl | 3-methoxyphenyl | Me—I |
| 4-(trifluoromethyl)phenyl | 3,4-difluorophenyl | 2,3-dihydro-1,4-benzodioxin-6-yl | Me-CH₂—I |

TABLE 1-continued

| R | R'—X |
|---|---|
| (structures) | (structures) |

In addition to 3-nitro-benzofurans, other core structures are also contemplated including, but not limited to, the following structures.

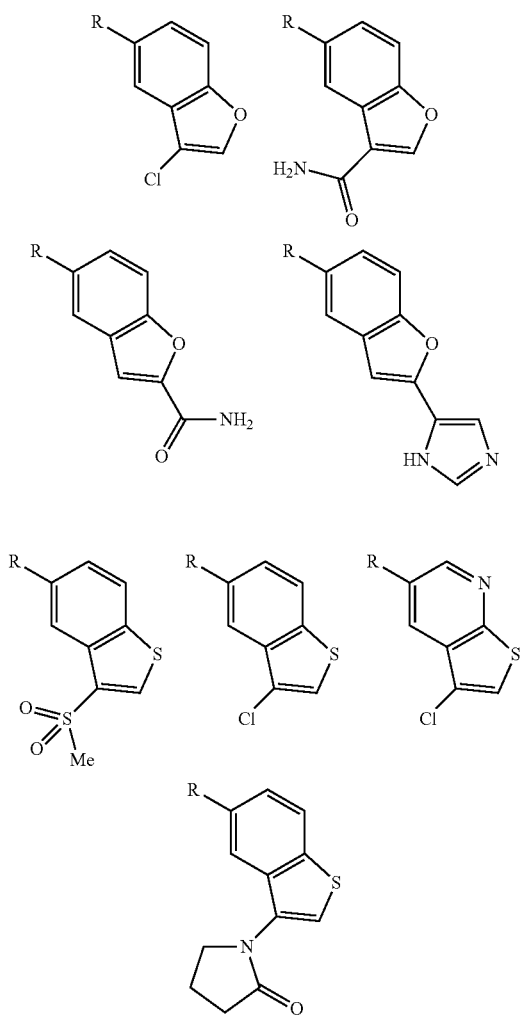

Example 2

Materials and Methods

Expression and Purification of Recombinant EBNA1 DBD.

Amino acids 454 to 607 of EBNA1 (GENBANK Accession No. YP_401677; SEQ ID NO:1), encoding the DNA binding domain were expressed as a hexa-histidine fusion protein in *E. coli*. Expression was induced in Rosetta2 cells with 0.3 mM IPTG for 3 hours at 25° C. Soluble protein was recovered and purified via Ni-NTA agarose according to standard methods (Frangioni & Neel (1993) *Anal. Biochem.* 210: 179-87). Bound protein was extensively washed with 20 mM HEPES, pH 7.9, 1 M NaCl, 5 mM 2-mercaptoethanol, 40 mM imidazole and 10% glycerol to dissociate nonspecific DNA bound to EBNA1 prior to elution in buffer containing 250 mM imidazole. Peak fractions of the eluted proteins were pooled and dialyzed against 20 mM HEPES, pH 7.9, 500 mM NaCl, 5 mM 2-mercaptoethanol, 10% glycerol, and 0.2 mM PMSF.

FP Assay.

The FP assay employed a probe with a non-palindromic site having two high-affinity half sites (5'-GGG TAG CAT ATG CTA TCT aga tag cat atg cta ccc-3'; SEQ ID NO:2). This probe bound EBNA1 with similar efficiency in EMSA (electrophoretic mobility shift assay), but performed significantly better in the FP (fluorescence polarization) assay. A reaction mix was prepared containing 200 mM NaCl, 20 mM Tris-Cl pH 7.4, 1 mM DTT, 10 μg/mL BSA, and 5 nM CY5-labeled EBNA1 BS Hairpin (opl 3016) or 5 nM FITC-labeled EBNA1 BS Hairpin (opl 4624), with or without 246 to 100 nM purified EBNA1 DNA Binding Domain. This solution was incubated for 30 minutes at room temperature to ensure binding. Thirty μL of this solution was dispensed to each well of the test plate with the compounds using a BIOTEK MICROFLO Select Dispenser. The plate was then centrifuged at 165×g to ensure the solution settled in the wells and incubated for 30 minutes at 25° C. The plate was then analyzed using a PERKIN ELMER 2104 Multilabel Reader.

EMSA Assay.

An EMSA reaction buffer was prepared containing 20% glycerol, 200 mM NaCl, 20 mM Tris-Cl pH 7.4, 1 mM DTT, 10 μg/mL BSA, and 10 nM CY5-labeled EBNA1 BS Hairpin (opl 3016), with or without 246 nM purified EBNA1 DNA Binding Domain. This solution was incubated for 20 minutes at room temperature to ensure binding. Thirty μL of this solution was dispensed to EPPENDORF tubes containing 0.5 μL of a test compound in DMSO and subsequently mixed. Samples were then loaded onto a 6% polyacrylamide gel and electrophoresed for 90 minutes at 170V. The gel was then scanned for fluorescence using a General Electric TYPHOON Imager.

FP Screening.

For initial screening, 2 μl of test compounds resuspended in DMSO were plated in triplicate wells in a black PERKIN ELMER OPTIPLATE at a concentration of 50 mM to achieve a final concentration of 3.33 mM when resuspended in 30 μL of reaction solution. The plate was assayed using the FP assay described herein. Specifically, 30 μl of a preformed EBNA1:CY5- or FITC-DNA hairpin complex was dispensed to wells containing candidate compounds. After a 1 hour incubation at room temperature, fluorescence polarization (EX: 620, EM: 680) was measured using an ENVISION XCITE Multilabel Reader (PERKIN ELMER). Percent inhibition of EBNA1 DNA binding was calculated for each compound relative to assay plate control wells (i.e., % inhibition=$(mP_{Max}-mP_{Cmpd})/(mP_{Max}-mP_{min})\times100$). Upon deconvulution, results were stratified into four categories: actives (i.e., the bioactive compound displayed >15% inhibition of EBNA1 DNA binding and cleanly mapped to a unique well in both the horizontal and vertical dimensions), ambiguous (i.e., the bioactive compound mapped to 2 or more wells in either dimension), orphan (i.e., an orthogonal match could not be identified in the second dimension), and inactive (<15% inhibition of EBNA1 DNA binding activity).

$IC_{50}$ Determination.

To determine $IC_{50}$ values, a 10-point 3-fold titration of each compound in 100% (v/v) DMSO was performed in duplicate starting at an initial concentration of 10 mM using a PERKIN ELMER JANUS to create a master plate. From this master plate, 0.5 μL was transferred to black PERKIN ELMER OPTIPLATE test plates with a PERKIN ELMER JANUS or to EPPENDORF tubes manually. The plate was assayed using the FP assay herein and the tubes assayed using the EMSA protocol described above.

EBNA1 Transcription Derepression Assay.

293T cells were seeded in 10-cm plates in DMEM media with 10% FBS. Following a 18-hour incubation at 37° C. to allow cells to adhere, cells at 50-70% confluence were transfected using 40 μL LIPOFECTAMINE (INVITROGEN) per plate. The cells were transfected with a 4 μg Qp-luciferase reporter plasmid (N1852) and 0.125 μg EBNA1 expression plasmid (N803) or 4 μg Qp-luciferase reporter plasmid (N1852) and 0.125 μg control plasmid (N799) (no EBNA) per plate. After 24 hours, the cells were harvested without trypsin, centrifuged 1200 RPM for 5 minutes and resuspended in DMEM media with 10% FBS at a concentration 100,000 cells per milliliter. Forty μL of this solution (40,000 cells) was dispensed to each well of the white plate using a BIOTEK MICROFLO Select Dispenser. Test compounds were added to achieve a final concentration range of 125 μM-2 nM, as described above. Cells were incubated at 37° C. for 48 hours, harvested and analyzed for luciferase activity using the PROMEGA STEADY-GLO luciferase system and read using a PERKIN ELMER 2104 Multilabel Reader.

EBV-Positive Selective Killing Assay.

To determine if the compounds were selectively killing EBV-positive cells, the viability of EBV-positive cells (LCLs, Mutul, Raji) were compared with EBV-negative cells (DG75 or BCBL1). Cells were resuspended at a concentration of 100,000 cells per milliliter and 40 μl (40,000 cells) of the resuspension was dispensed to each well of a 384-well clear plate. Test compounds (0.5 μl) were added to each well to achieve a final concentration range of 125 μM-2 nM. After incubating the cells at 37° C. for 72 hours with the compounds, the cells were analyzed using the PROMEGA MTS reagent and read using a PERKIN ELMER 2104 Multilabel Reader.

Xenograft Mouse Model Assay.

To test the efficacy of compounds in vivo, a xenograft mouse model was developed in an immunodeficient NOD SCID (NOD.CB17-Prkdcscid/NcrCrl) mouse (The Jackson Laboratory). Mutu LCL cells were transduced with a lentivirus (N1893) that constitutively expressed GFP and luciferase and sorted using a flow cytometer to isolate a population of cells that express GFP and luciferase. Five million transduced Mutu LCL GFP/luciferase-positive cells were suspended in 100 μl sterile PBS and injected subcutaneously into the right flank of six week old female NOD SCID mice. Test compounds were formulated in vehicle (5% n-methylpyrollidone, 45% SOLUTOL HS 15, and 50% 1% LUTROL F 68 in water) and sterile filtered. Test compounds were dosed intraperitoneal once a day on days 7, 9, and 11. On days 9, 14, 18, 21, 23, and 25, tumor size was measured using the IVIS Imager. For these measurements each animal was anesthetized with isofluorane and injected intraperitoneal with 250 μl of a 15 mg/ml stock of D-luciferin firefly, potassium salt (GOLD BIOTECHNOLOGY, #LUCK1G, dissolved in DPBS) per gram of body weight. After 20 minutes, mice were placed in the XENOGEN IVIS imager (CALIPER LIFESCIENCES) and tumor size was read using total flux as the measurement value.

Example 3

Activity of Compounds

Compounds were screened for activity in the cell-based assay disclosed herein. The $IC_{50}$ values of the compounds are listed in Table 2.

TABLE 2

| Formula | Compound | Compound Structure | $IC_{50}$ (nM) |
|---|---|---|---|
| I | VKE01441 | Cl-phenyl-O-C(=O)-benzofuran | 9061 |

TABLE 2-continued
| Formula | Compound | Compound Structure | IC$_{50}$ (nM) |
|---|---|---|---|
| I | VKE01442 | 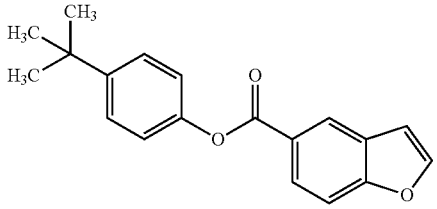 [SMILES: CC(C)(C)c1ccc(OC(=O)c2ccc3occc3c2)cc1] | 2634 |
| II | VKE01443 | 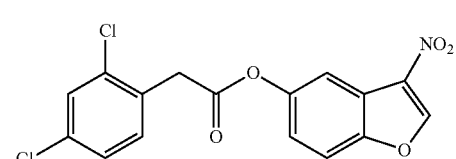 | 125000 |
| II | VKE01444 | 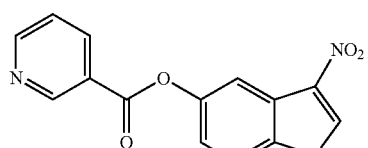 | 125000 |
| II | VKE01445 | 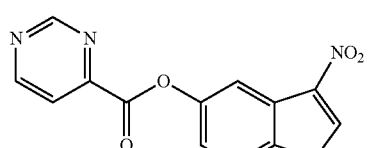 | 125000 |
| II | VKE01446 | 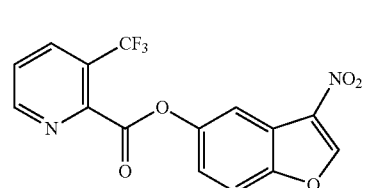 | 125000 |
| II | VKE01447 | 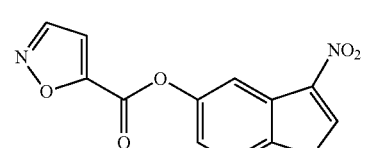 | 125000 |
| II | VKE01448 | 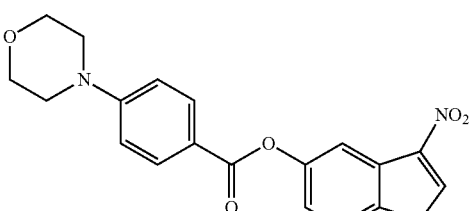 | 30570 |
| II | VKE01449 | 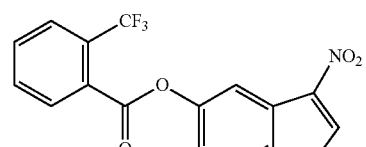 | 125000 |

TABLE 2-continued
| Formula | Compound | Compound Structure | IC₅₀ (nM) |
|---|---|---|---|
| II | VKE01450 | 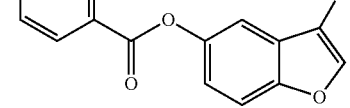 | 9016 |
| II | VKE01451 | 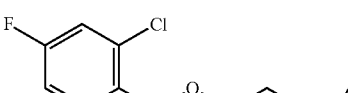 | 3283 |
| II | VKE01452 | 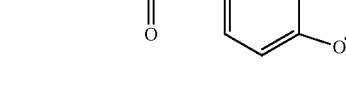 | 125000 |
| II | VKE01453 | 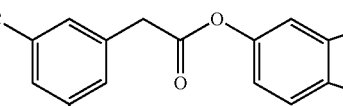 | 1244 |
| II | VKE01454 |  | 9779 |
| II | VKE01455 | 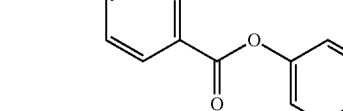 | 27150 |
| II | VKE01456 |  | 14010 |
| III | VKE01457 | 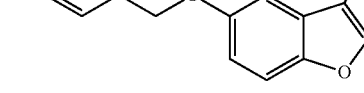 | 18.95 |

TABLE 2-continued
| Formula | Compound | Compound Structure | IC$_{50}$ (nM) |
|---|---|---|---|
| III | VKE01458 | 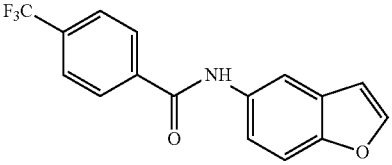 [SMILES: O=C(Nc1ccc2occc2c1)c1ccc(C(F)(F)F)cc1] | 4.762 |
| III | VKE01459 | 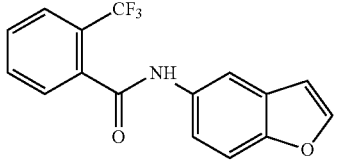 [SMILES: O=C(Nc1ccc2occc2c1)c1ccccc1C(F)(F)F] | 6523 |
| III | VKE01460 | 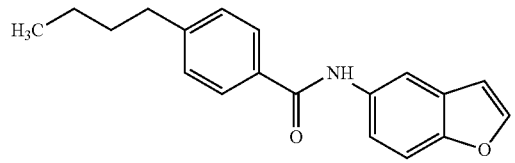 [SMILES: CCCCc1ccc(C(=O)Nc2ccc3occc3c2)cc1] | 12.34 |
| III | VKE01461 | 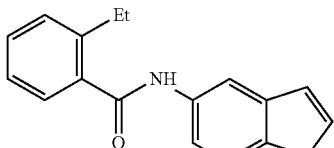 | 1015 |
| III | VKE01462 | 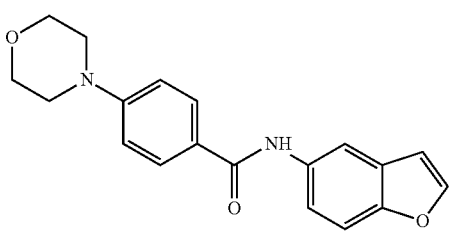 [SMILES: O=C(Nc1ccc2occc2c1)c1ccc(N2CCOCC2)cc1] | 298.1 |
| III | VKE01463 | 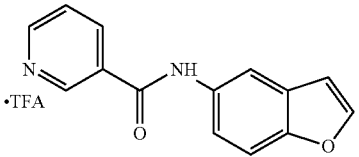 [SMILES: O=C(Nc1ccc2occc2c1)c1cccnc1] | 1259 |
| III | VKE01464 | 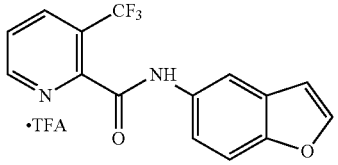 [SMILES: O=C(Nc1ccc2occc2c1)c1ncccc1C(F)(F)F] | 1092 |
| III | VKE01465 | 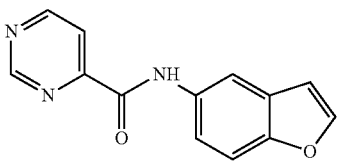 [SMILES: O=C(Nc1ccc2occc2c1)c1ccncn1] | 1655 |

TABLE 2-continued

| Formula | Compound | Compound Structure | IC$_{50}$ (nM) |
|---|---|---|---|
| III | VKE01466 | (isoxazole-5-carboxamide-N-benzofuran-5-yl) | 83810 |
| I | VKE01467 | (2-fluorophenyl benzofuran-5-carboxamide) | 673.6 |
| I | VKE01468 | (3-chlorophenyl benzofuran-5-carboxamide) | 813.1 |
| I | VKE01469 | (4-tert-butylphenyl benzofuran-5-carboxamide) | 62.72 |
| I | VKE01470 | (4-chloro-3-methylphenyl benzofuran-5-carboxamide) | 42.05 |
| I | VKE01471 | (3,4-difluorophenyl benzofuran-5-carboxamide) | 847.1 |
| I | VKE01472 | (pyridin-2-yl benzofuran-5-carboxamide · TFA) | 152.3 |
| I | VKE01473 | (TFA · pyridin-4-yl benzofuran-5-carboxamide) | 20830 |

TABLE 2-continued

| Formula | Compound | Compound Structure | IC$_{50}$ (nM) |
|---|---|---|---|
| I | VKE01474 | H$_3$C-(4-methylthiazol-2-yl)-NH-C(=O)-benzofuran-5-yl | 60.25 |

Compounds with IC$_{50}$s of 125000 nM were not active.

What is claimed is:

1. A method for inhibiting the activity of Epstein-Barr Nuclear Antigen 1 (EBNA1) protein comprising contacting an EBNA1 protein with an effective amount of a compound of Formula III:

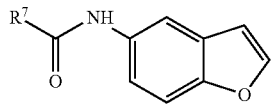

Formula III wherein $R^7$ is a substituted or unsubstituted phenyl, pyridyl, or pyrimidinyl group, so that the activity of the EBNA1 protein is inhibited.

2. A method for treating a latent Epstein-Barr virus infection comprising administering to a subject having a latent Epstein-Barr virus infection a pharmaceutical composition comprising a pharmaceutically acceptable carrier and a compound of Formula III:

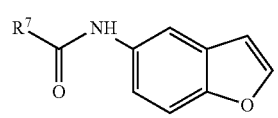

Formula III wherein $R^7$ is a substituted or unsubstituted phenyl, pyridyl, or pyrimidinyl group, so that the subject's latent Epstein-Barr virus infection is treated.

3. The method of claim 2, wherein the latent Epstein-Barr virus infection is associated with cancer.

* * * * *